(12) United States Patent
Imai et al.

(10) Patent No.: US 11,642,151 B2
(45) Date of Patent: May 9, 2023

(54) REMOVAL DEVICE AND REMOVAL SYSTEM

(71) Applicant: TERUMO KABUSHIKI KAISHA, Tokyo (JP)

(72) Inventors: Masaomi Imai, Kofu (JP); Takashi Kitaoka, Hadano (JP); Kazuaki Kanamoto, Hadano (JP); Yuki Masubuchi, Hadano (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 54 days.

(21) Appl. No.: 17/016,847

(22) Filed: Sep. 10, 2020

(65) Prior Publication Data

US 2020/0405346 A1    Dec. 31, 2020

Related U.S. Application Data

(63) Continuation of application No. PCT/JP2019/007440, filed on Feb. 27, 2019.

(30) Foreign Application Priority Data

Mar. 13, 2018 (JP) .............................. JP2018-045179

(51) Int. Cl.
*A61B 17/3207* (2006.01)
*A61B 17/32* (2006.01)

(52) U.S. Cl.
CPC ................ *A61B 17/320758* (2013.01); *A61B 17/32002* (2013.01); *A61B 2017/320024* (2013.01); *A61B 2217/005* (2013.01)

(58) Field of Classification Search
CPC ...... A61B 17/320758; A61B 17/32002; A61B 2017/320024; A61B 2217/005
See application file for complete search history.

(56) References Cited

U.S. PATENT DOCUMENTS

| 4,315,511 A | 2/1982 | Chin |
| 4,621,636 A | 11/1986 | Fogarty |
| 5,662,603 A | 9/1997 | Gelbfish |

(Continued)

FOREIGN PATENT DOCUMENTS

| JP | H10-057388 A | 3/1998 |
| JP | 2002510517 A | 4/2002 |

(Continued)

OTHER PUBLICATIONS

The extended European Search Report dated Apr. 20, 2021, by the European Patent Office in corresponding European Patent Application No. 19768453.3-1113. (11 pages).

(Continued)

*Primary Examiner* — Ashley L Fishback
(74) *Attorney, Agent, or Firm* — Buchanan Ingersoll & Rooney PC

(57) ABSTRACT

A removal device and a removal system are configured to effectively remove an object in a body lumen while suppressing damage to another device. The removal device includes an elongated shaft part, and a cutting part fixed to a distal portion of the shaft part. The proximal portion of the cutting part includes a ring-shaped cutting blade, and a surface of the cutting part on which the cutting blade is positioned is inclined relative to center axis of the shaft part at an angle greater than 0 degrees and less than 90 degrees.

11 Claims, 7 Drawing Sheets

(56) References Cited

U.S. PATENT DOCUMENTS

| | | |
|---|---|---|
| 8,366,735 B2 | 2/2013 | Bose et al. |
| 2007/0265647 A1 | 11/2007 | Bonnette et al. |
| 2016/0331506 A1 | 11/2016 | Korkuch et al. |
| 2016/0354107 A1 | 12/2016 | Nakano et al. |
| 2019/0183519 A1 | 6/2019 | Imai et al. |

FOREIGN PATENT DOCUMENTS

| | | |
|---|---|---|
| JP | 2014533131 A | 12/2014 |
| JP | 2018033491 A | 3/2018 |
| WO | 2007/072043 A1 | 6/2007 |
| WO | 2011/128934 A1 | 10/2011 |
| WO | 2016/161095 A1 | 10/2016 |
| WO | 2018/043282 A1 | 3/2018 |

OTHER PUBLICATIONS

International Search Report (PCT/ISA/210) dated May 7, 2019, by the Japanese Patent Office as the International Searching Authority for International Application No. PCT/JP2019/007440.

Written Opinion (PCT/ISA/237) dated May 7, 2019, by the Japanese Patent Office as the International Searching Authority for International Application No. PCT/JP2019/007440.

An English Translation of the International Search Report (Form PCT/ISA/210) and the Written Opinion of the International Searching Authority (Form PCT/ISA/237) dated May 7, 2019, by the Japanese Patent Office in corresponding International Application No. PCT/JP2019/007440. (6 pages).

Office Action (Notice of Reasons for Refusal) dated Sep. 5, 2022, by the Japan Patent Office in corresponding Japanese Patent Application No. 2020-505745 and an English Translation of the Office Action. (9 pages).

FIG.1
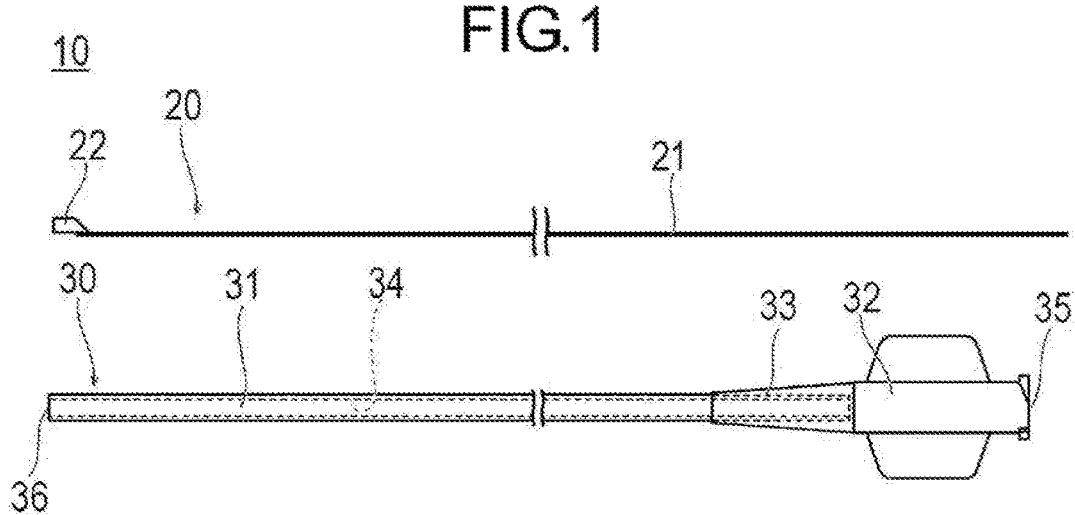
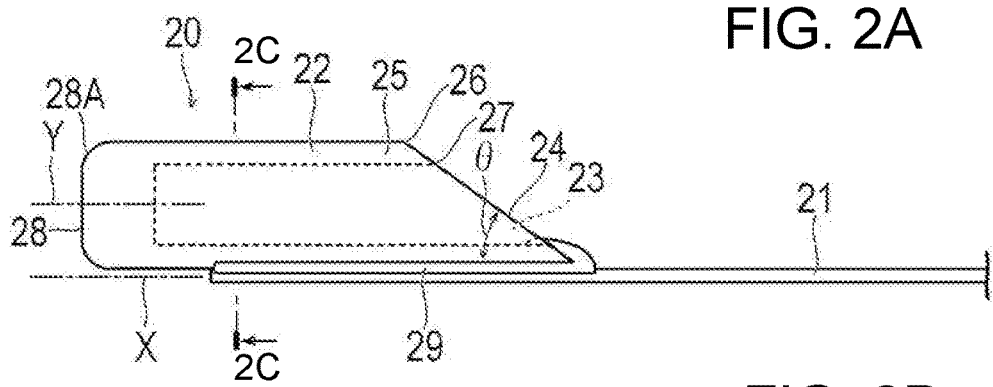
FIG. 2A
FIG. 2B
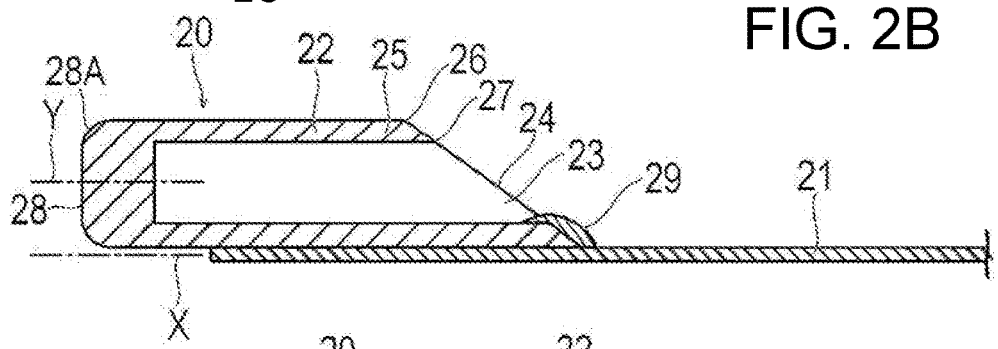
FIG. 2C
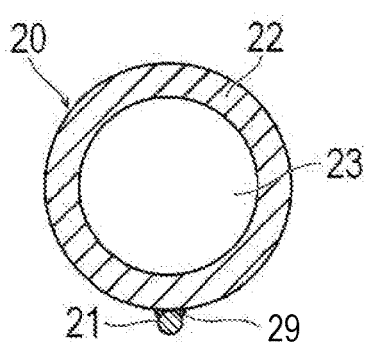

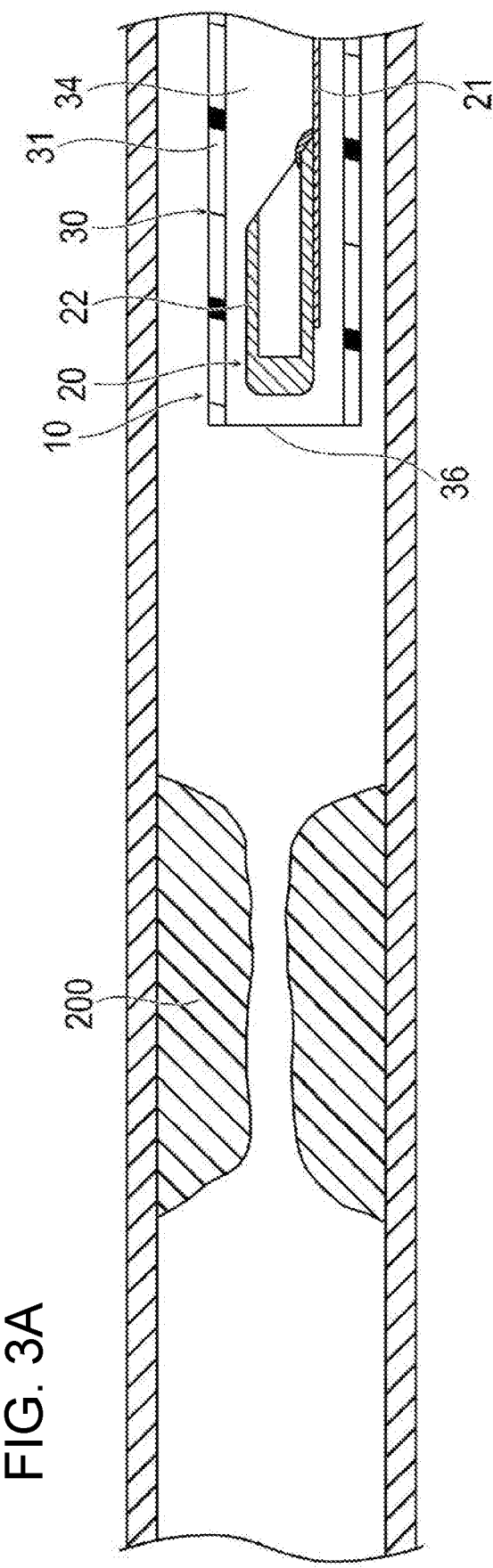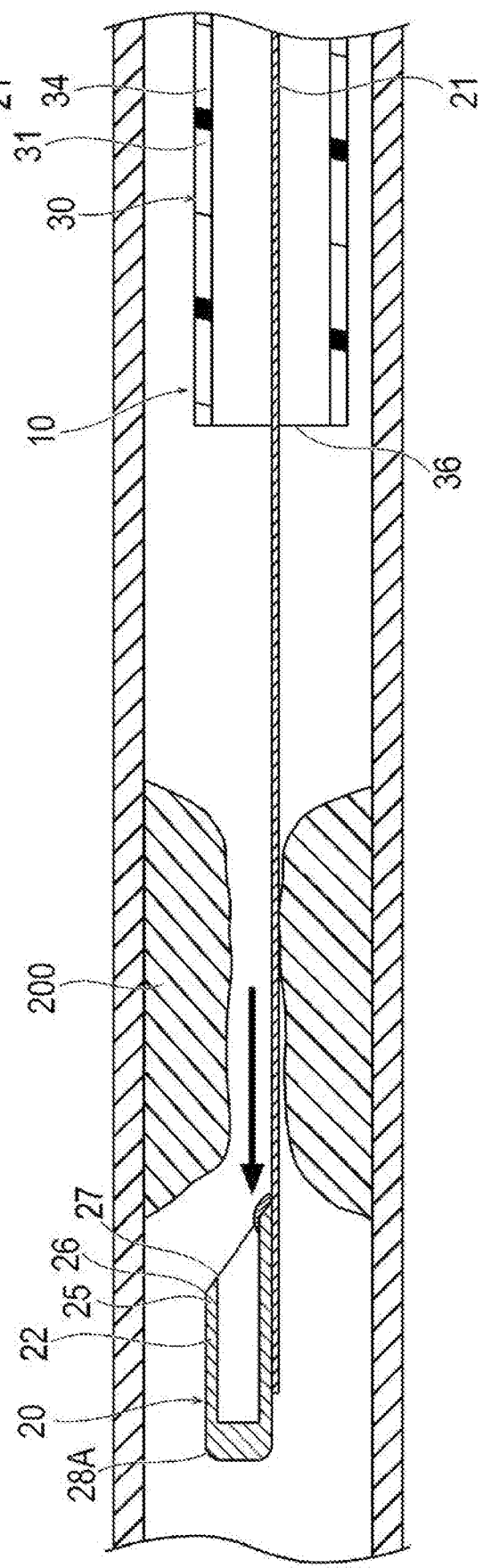
FIG. 3A
FIG. 3B

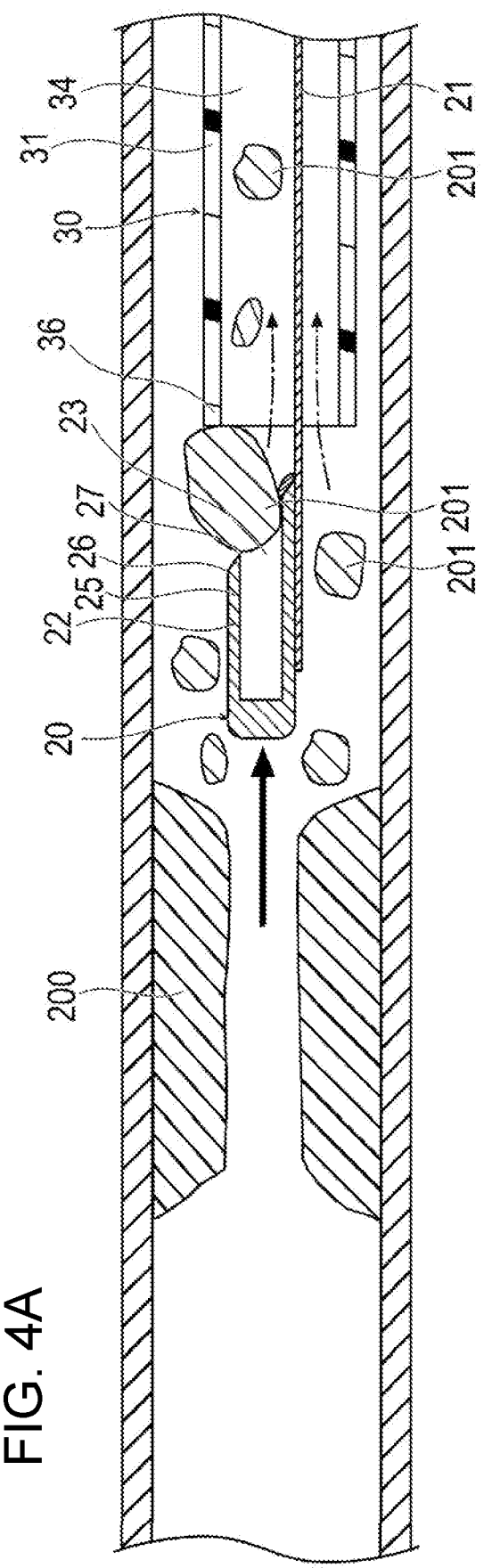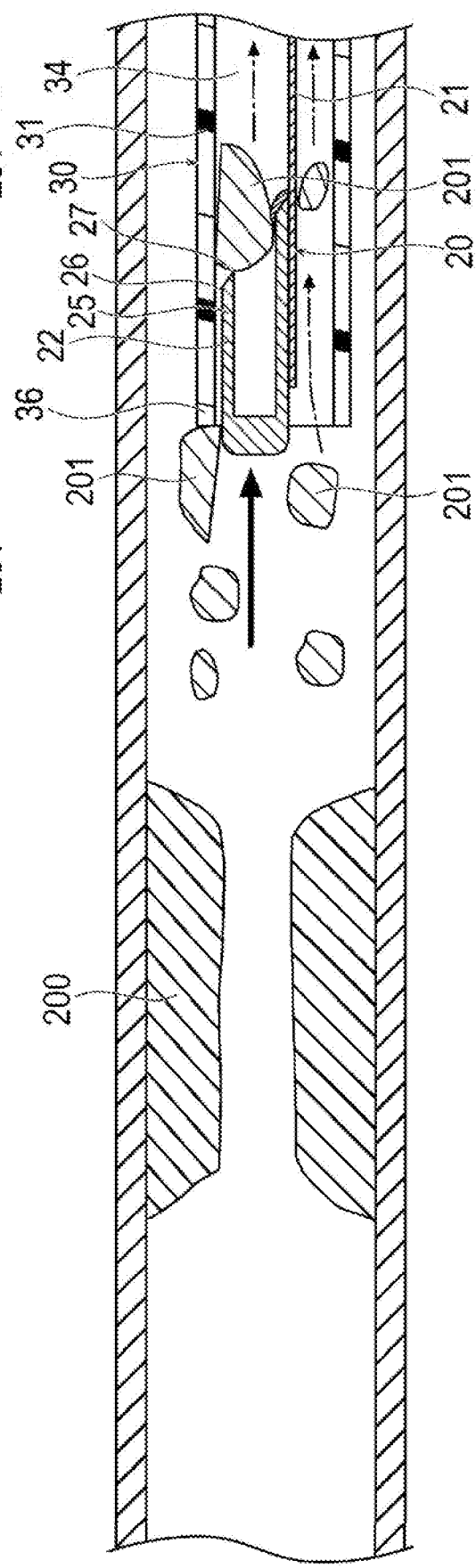

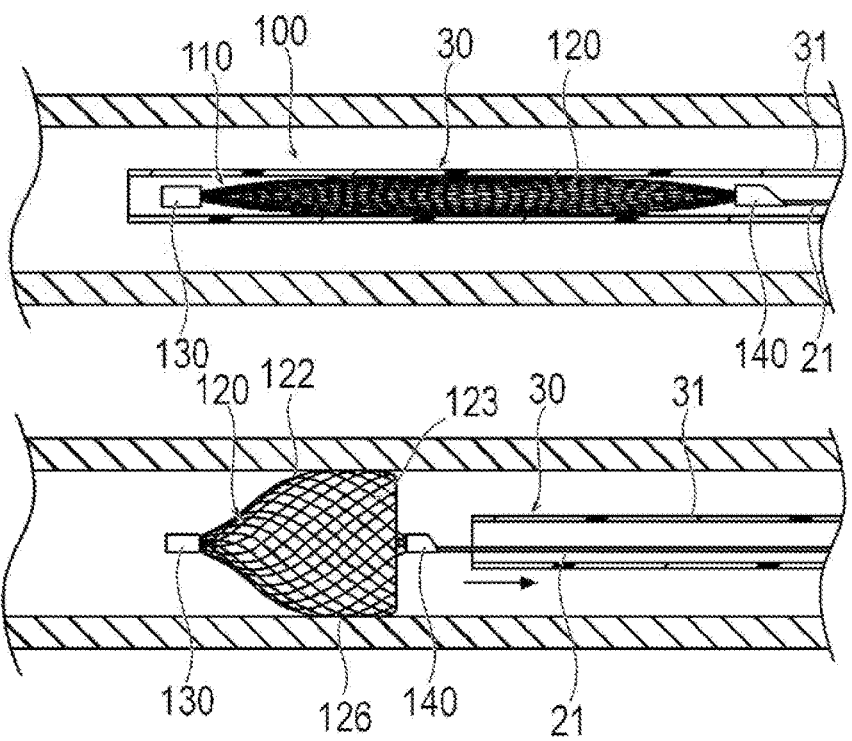
FIG. 8A
FIG. 8B
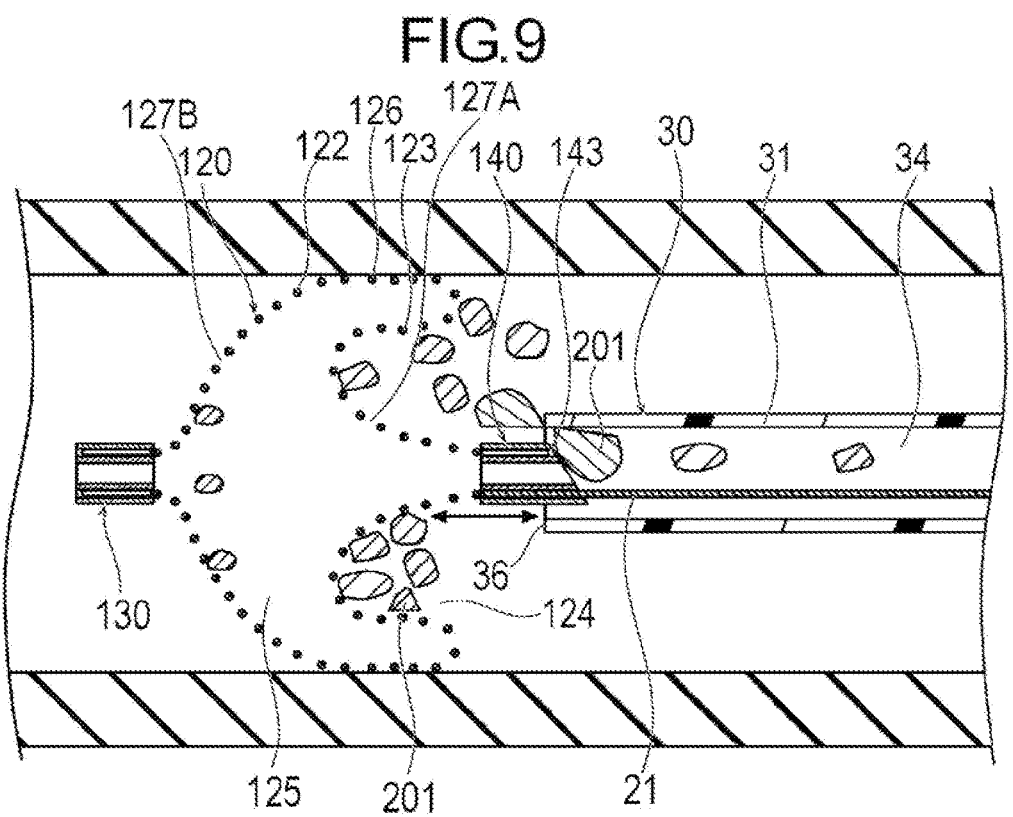
FIG. 9

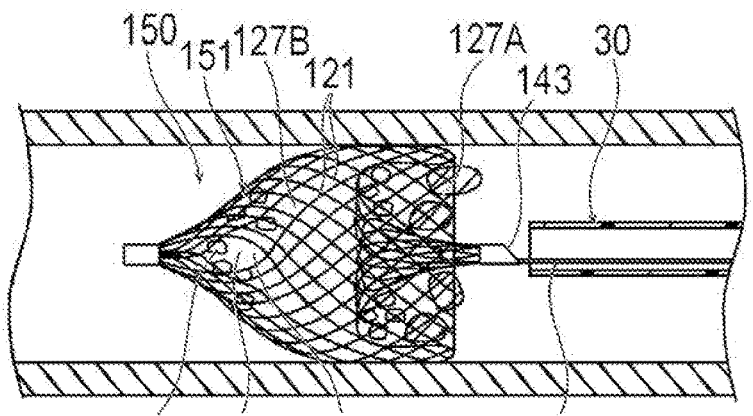
FIG. 10A
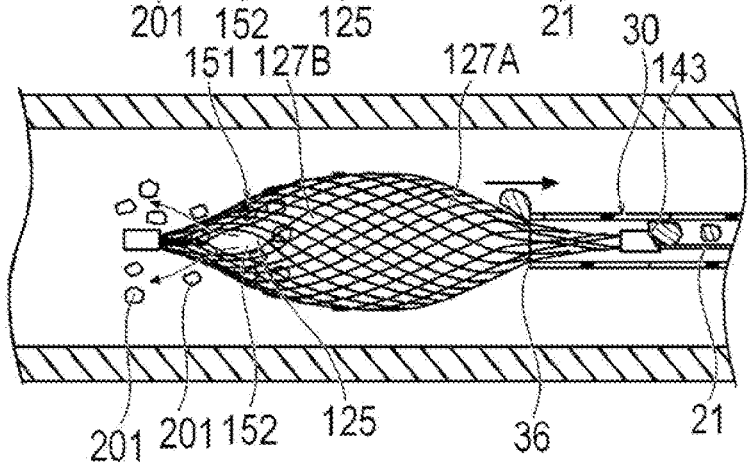
FIG. 10B
FIG. 11A
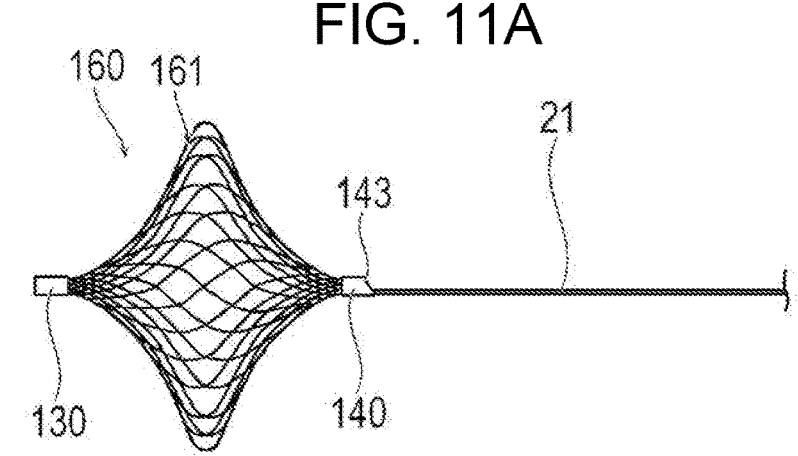
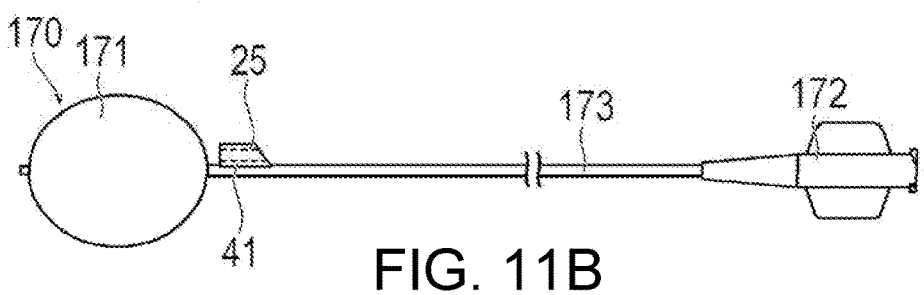
FIG. 11B

REMOVAL DEVICE AND REMOVAL SYSTEM

CROSS-REFERENCES TO RELATED APPLICATIONS

This application is a continuation of International Application No. PCT/JP2019/007440 filed on Feb. 27, 2019, which claims priority to Japanese patent Application No. 2018-045179 filed on Mar. 13, 2018, the entire content of both of which is incorporated herein by reference.

FIELD OF THE INVENTION

This invention generally relates to a removal device and a removal system that remove an object in a body lumen.

BACKGROUND DISCUSSION

When a thrombus is formed in a blood vessel, it is difficult for blood to flow to a periphery side of the thrombus. This prevents oxygen and nutrition from sufficiently reaching the periphery, and there is a danger of necrosis of cell tissue that has become depleted of oxygen. Therefore, for example, U.S. Pat. No. 8,366,735 describes a device that aspirates and removes thrombi by a sheath connected to an aspirating pump. This device is provided with a separator that can protrude from a tip opening of the sheath. The separator is provided to a distal portion of a wire that penetrates through the sheath, and has an outer diameter larger than that of the wire. An operator causes the separator to protrude from the tip opening of the sheath and moves the separator in the front-back direction to allow the thrombi to be led into the sheath.

SUMMARY

However, in a case where a thrombus is hard and large, the device described in U.S. Pat. No. 8,366,735 cannot lead the thrombus into the sheath.

Disclosed here is a removal device and a removal system that can effectively remove an object in a body lumen while suppressing damage to another device.

The removal device includes: an elongated shaft part possessing a proximal portion and a distal portion at opposite axial ends of the elongated shaft part, with the elongated shaft part possessing a center axis and being axially movable; a cutting part fixed to the distal portion of the shaft part so that the cutting part and the elongated shaft part move together when the elongated shaft part is axially moved, with the cutting part including a distal portion and a proximal portion and the proximal portion of the cutting part being positioned axially closer to the proximal portion of the elongated shaft part than the distal portion of the cutting part. The proximal portion of the cutting part includes a ring-shaped cutting blade, with the cutting blade positioned on a surface that is inclined relative to the center axis of the elongated shaft part at an angle of more than 0 degrees and less than 90 degrees.

The removal system includes an elongated sheath that includes a lumen possessing an open distal end and an open proximal end, wherein the lumen is connectable to an aspirating device that produces an aspiration force in the lumen; an elongated shaft part possessing a proximal portion and a distal portion at opposite axial ends of the elongated shaft part, with the elongated shaft part possessing a center axis and the elongated shaft part being positionable in the lumen of the elongated shaft part and being axially movable relative to the elongated shaft part; and a cutting part that is fixed to the distal portion of the elongated shaft part so that the cutting part and the elongated shaft part move together when the elongated shaft part is axially moved. The cutting part includes a distal portion and a proximal portion, with the proximal portion of the cutting part being positioned axially closer to the proximal portion of the elongated shaft part than the distal portion of the cutting part. The proximal portion of the cutting part includes a ring-shaped cutting blade, with the cutting blade being positioned on a surface that is inclined relative to the center axis of the elongated shaft part at an angle of more than 0 degrees and less than 90 degrees.

According to another aspect, a method of removing an object from a lumen in a living body comprises: inserting a cutting part into the lumen in the living body, wherein the cutting part is fixed to an elongated shaft part so that movement of the elongated shaft part results in movement of the cutting part, and the cutting part includes a distal portion and a proximal portion, with the proximal portion of the cutting part including a ring-shaped cutting blade. The method also includes: moving the cutting part in a distal direction in the lumen in the living body toward the object in the lumen in the living body by moving the elongated shaft part in the distal direction; moving the cutting part in the distal direction in the lumen in the living body to move the cutting part from a proximal side of the object in the lumen in the living body to a distal side of the object in the lumen in the living body; moving the cutting part that is located on the distal side of the object in a proximal direction in the lumen in the living body to cause the cutting blade to cut the object and produce a cut object in the lumen in the living body; and aspirating the cut object in the lumen in the living body to remove the cut object from the lumen in the living body.

The removal device and the removal system configured as above insert the cutting part into the body lumen and then pull the shaft part to allow the cutting blade to cut an object in the body lumen. The cutting blade having a ring shape receives a part of an object having a three-dimensional shape in an inside of the ring, and is thus easy to be caught by the object. Therefore, the removal device and the removal system can effectively cut and remove the object by the cutting blade that is difficult to slip with respect to the object. The surface on which the cutting blade is positioned is inclined relative to the center axis of the shaft part at an angle of less than 90 degrees, so that the cutting blade is difficult to damage another device, for example, the sheath, when moving to the proximal side.

BRIEF DESCRIPTION OF THE DRAWINGS

FIG. 1 is a plan view illustrating a removal system according to a first embodiment.

FIGS. 2(A)-2(C) depict views illustrating a distal portion of a removal device in the first embodiment: FIG. 2(A) is a plan view; FIG. 2(B) is a cross-sectional view; and FIG. 2(C) is a cross-sectional view along the section line 2A-2A in FIG. 2(A).

FIGS. 3(A) and 3(B) depict cross-sectional views illustrating states in a blood vessel: FIG. 3(A) illustrates a state where the removal system is inserted into the blood vessel; and FIG. 3(B) illustrates a state where the removal device is caused to protrude from a sheath.

FIGS. 4(A) and 4(B) depict cross-sectional views illustrating states in the blood vessel: FIG. 4(A) illustrates a state where thrombi are caused to fall off from a body lumen by the removal device; and FIG. 4(B) illustrates a state where the fallen-off thrombus are being led into the sheath.

FIG. 5(A) illustrates a first modification example; FIG. 5(B) illustrates a second modification example; FIG. 5(C) illustrates a third modification example; FIG. 5(D) illustrates a fourth modification example; and FIG. 5(E) illustrates a fifth modification example.

FIGS. 8(A) and 8(B) depict cross-sectional views illustrating states in a blood vessel: FIG. 8(A) illustrates a state where the removal device is inserted into the blood vessel; and FIG. 8(B) illustrates a state where an inflating part is indwelt in the blood vessel.

FIG. 9 is a cross-sectional view illustrating a state where the thrombi cut by the removal device are being led into the sheath.

FIGS. 10(A) and 10(B) depict cross-sectional views illustrating a sixth modification example of a removal device; FIG. 10(A) illustrates a state where an inflating part of the removal device is disposed in a blood vessel; and FIG. 10(B) illustrates a state where the inflating part is caused to deflate and is recovered into a sheath.

FIGS. 11(A) and 11(B) depict plan views illustrating modification examples of the removal device: FIG. 11(A) illustrates a seventh modification example; and FIG. 10 FIG. 11(B) illustrates an eighth modification example.

DETAILED DESCRIPTION

Figure 5A:
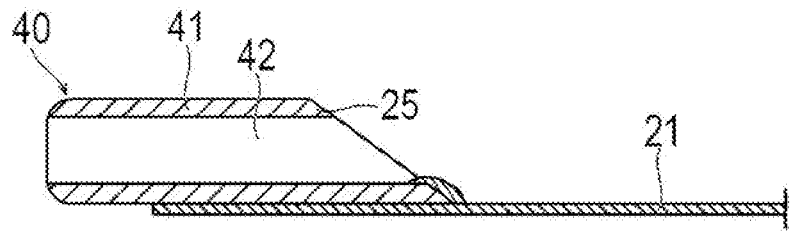
FIGS. 5(A)-5(E) cross-sectional views illustrating modification examples of the removal device.

Set forth below with reference to the accompanying drawings is a detailed description of embodiments of a removal device, a removal system and a manner of operation representing examples of the inventive removal device, removal system and operational method disclosed here. The dimensions or scales on the drawings may be exaggerated or different from actuality/reality for convenience of description and illustration.

First Embodiment

A removal system 10 according to a first embodiment representing one example of the inventive removal device and removal system may be used to aspirate and remove an object such as a thrombus, plaque, or a calcified lesion in a blood vessel. In the description that follows, a side or end of the device to be inserted into a blood vessel is referred to as a "distal side" or "distal end", and a hand-side (opposite side or end) where the device is operated is referred to as a "proximal side" or "proximal end". Moreover, an object to be removed is not necessarily limited to a thrombus, plaque, or a calcified lesion, as the removal device and removal system disclosed here has useful application to remove all objects that can exist in a body lumen. In addition, in the description that follows, a source side of a flow in the blood vessel is referred to as an "upstream side", and a side toward which the flow of blood is headed is referred to as a "downstream side".

The removal system 10 includes the combination of a removal device 20 that cuts an object in the blood vessel, and a sheath 30 configured to store therein the removal device 20, as illustrated in FIGS. 1 and 2. The removal device 20 includes an axially movable elongated shaft part 21, and a main cutting body part 22 that is fixed to a distal portion of the shaft part 21 so that the main cutting body part 22 and the elongated shaft part 21 move together when the elongated shaft part 21 is axially moved.

The shaft part 21 is an elongated wire that extends from a hand side (proximal end) to the main cutting body part 22. The distal portion of the shaft part 21 is fixed to the main cutting body part 22.

A constituent material from which the shaft part 21 may be fabricated is not specially limited but preferably has a tensile strength to some extent. Examples of the material from which the shaft part 21 may be fabricated include stainless steel, a shape memory alloy, and the like. As for a shape memory alloy, Ni—Ti-based, Cu—Al—Ni-based, Cu—Zn—Al-based shape memory alloys, combinations thereof, and the like are preferably used. The shaft part 21 is not limited to a solid wire, but may be a hollow tubular body, for example.

The main cutting body part 22 is an approximately cylindrical member having an outer diameter larger than that of the shaft part 21. In the main cutting body part 22, a concave portion or recessed (hollow) portion 23 that is closed at the distal side and is opened toward the proximal side is formed. The main cutting body 22 thus has a closed distal end and an open proximal end. An end portion on the proximal side of the main cutting body part 22 is sloped so that the main cutting body includes a slope (sloped proximal end surface) 24 that is inclined at an angle θ of less than 90 degrees (interior angle) relative to a center axis or central axis X of the shaft part 21. In other words, a proximal portion of the main cutting body part 22 has a shape in which a cylinder having an inner diameter and an outer diameter that are constant in an axial direction is obliquely cut. The inclined angle θ exceeds 0 degrees and is less than 90 degrees, and is preferably between 20 degrees and 80 degrees, more preferably between 30 degrees and 60 degrees. The main cutting body part 22 and the shaft part 21 are arranged such that a part that is positioned at the most proximal side of the slope 24 is adjacent to the shaft part 21. That is, as shown in FIGS. 2(A) and 2(B), the sloped proximal end surface of the main cutting body part 22 slopes upwardly and in the distal direction away from the shaft part 21. The concave portion 23 opens to the slope or sloping surface 24. A ring-shaped or annular-shaped region that surrounds the concave portion 23 of the slope 24 forms a cutting part 25. The cutting part 25 includes an outer edge 26 that is positioned at an outer peripheral surface side of the main cutting body part 22, and an inner edge 27 that is positioned at an inner peripheral surface side of the main cutting body part 22. The outer edge 26 and/or the inner edge 27 functions as a sharp cutting blade. Accordingly, the slope 24 is a surface on which the cutting blade is positioned. An end portion on the distal side or distal end of the main cutting body part 22 includes a distal surface or distal end surface 28. An outer peripheral portion 28A that is positioned radially outward of the distal surface 28 is subjected to curved surface processing so that the distal end portion possesses curved or rounded corners as shown in FIGS. 2(A) and 2(B), and is smoothly connected to an outer peripheral surface of the main cutting body part 22. The shape of the ring-shaped or annular-shaped sloped surface 24 may be an ellipse or a circle. A part of the surface (surface between the outer edge (outer periphery) and the inner edge (inner periphery)) of the ring may be partially thinned.

The outer peripheral surface of the main cutting body part 22 is fixed to the shaft part 21 by a fixing part 29. The fixing part 29 is formed, for example, by welding, soldering, brazing, an adhesive, or the like. The shaft part 21 is fixed to the main cutting body part 22 at a position that is spaced in the radial direction from a center axis or central axis Y of the main cutting body part 22 and the cutting part 25 (i.e., the center axis X of the elongated shaft part 21 and the center axis Y of the main cutting body part 22/cutting part 25 are not coaxial). The shaft part 21 does not need to be fixed to the outer peripheral surface of the main cutting body part 22. For example, the shaft part 21 may be fixed to an inner peripheral surface of the main cutting body part 22. Alternatively, the shaft part 21 may be fitted into a fitting hole that is formed in the sloped surface 24 of the main body cutting part 22 toward the distal side. In this case, the shaft part 21 is positioned between the inner peripheral surface and the outer peripheral surface of the main cutting body part 22. When the fixing part 29 abuts on a distal surface of the sheath 30, the cutting part 25 is positioned outward in a radial direction of the sheath 30 (e.g., the central axis Y of the cutting part 25 is positioned radially outwardly of the central axis of the sheath 30). At this time, the contact of the fixing part 29 with the distal surface of the sheath 30 can be further reduced (e.g., by virtue of the curved configuration of the fixing part 29). Accordingly, the cutting part 25 can be smoothly led into a lumen (a lumen 34, which is described later) of the sheath 30.

A constituent material from which the main cutting body part 22 may be fabricated is preferably hard to the extent that makes it difficult to damage biological tissue (e.g., a blood vessel wall) and the sheath 30, while also allowing an object such as thrombus to be cut. Examples of materials from which the main cutting body part 22 may be fabricated include engineering plastics such as polyether ether ketone (PEEK), polyamide (PA), polycarbonate (PC), polysulfone (PSU), and polyamideimide (PAI).

The sheath 30 includes a sheath main body 31, a hub 32, and an anti-kink protector 33, as illustrated in FIG. 1. The sheath main body 31 is provided with the lumen 34 configured to accommodate the removal device 20. The sheath main body 31 includes a sheath opening portion (sheath opening) 36 in an end portion on the distal side. The hub 32 is fixed to the proximal end portion of the sheath main body 31. The hub 32 is provided with a hub opening portion (hub opening) 35 that communicates with the lumen 34. The hub opening portion 35 can be connected with an aspirating device that generates an aspiration force via a Y connector or the like. The aspirating device may be, for example, a syringe, a pump, or the like. The hub opening portion 35 is connected with the Y connector to allow the aspirating device, in a state of an elongated device (for example, the shaft part 21) being inserted or positioned in the hub 32 and the sheath main body 31, to be connected thereto. Moreover, the hub opening portion 35 can also be connected with a syringe, the Y connector, or the like with which a thrombolytic agent and the like are supplied. The anti-kink protector 33 is a flexible member that covers an interlock part of the sheath main body 31 and the hub 32. The anti-kink protector 33 suppresses a kink of the sheath main body 31.

A constituent material from which the sheath main body 31 may be fabricated is not specifically limited. Examples of the constituent material from which the sheath main body 31 may be fabricated include polyolefin such as polyethylene, polypropylene, ethylene-propylene copolymer, or ethylene-vinyl acetate copolymer, polyvinyl chloride, polystyrene, polyamide, polyimide, or a combination thereof. The sheath main body 31 may be fabricated from a plurality of materials, or a reinforcing member such as a wire rod may be embedded therein.

Next, a method of using a removal device 10 according to the present embodiment will be described, considering as an example a situation in which a thrombus (object) in a blood vessel (body lumen) is aspirated and removed.

Firstly, an operator percutaneously inserts an introducer sheath into a blood vessel (lumen in a living body), at the upstream side (proximal side) from a thrombus in the blood vessel. Next, the operator inserts a guide wire into the blood vessel through this introducer sheath. Subsequently, the operator inserts a proximal side end portion of the guide wire (the proximal end portion of the guide wire located outside the living body) into the sheath opening portion or open distal end 36 of the sheath 30. Subsequently, the operator advances the sheath along the guide wire to cause the sheath 30 to reach the vicinity of the thrombus.

Subsequently, the operator extracts the guide wire from the sheath 30. The operator then connects the Y connector to the hub opening portion 35, and inserts the removal device 20 into the lumen 34 of the sheath 30 by way of the hub opening portion 35. Subsequently, the operator operates the shaft part 21 that is positioned outside of the body to move the main cutting body part 22 to the distal side (in the distal direction), as illustrated in FIG. 3(A).

Subsequently, the operator operates the shaft part 21 that is positioned outside the body to axially move the shaft part 21 in the forward or distal direction so that the main cutting body part 22 protrudes distally beyond the distal open end of the sheath 30. To cause the removal device 20 to reach a distal side of a thrombus 200 in the lumen of the living body, a separately prepared support catheter can also be used.

Subsequently, the operator operates the shaft part 21 to alternately move the main cutting body part 22 to the distal side (in the distal direction) and to the proximal side (in the proximal direction) along the blood vessel. More specifically, the operator operates the shaft part 21 to move the main cutting body part 22 from a position proximal of the thrombus 200 to a position distal of the thrombus, and from a position distal of the thrombus 200 to a position proximal of the thrombus. When the main cutting body part 22 moves to the distal side or in the distal direction, as illustrated in FIG. 3(B), the smooth outer peripheral portion 28A of the main cutting body part 22 comes into contact with the thrombus 200. Therefore, the main cutting body part 22 can excellently move through a clearance of the thrombus 200 to the distal side of the thrombus 200. When the main cutting body part 22, positioned on the distal side of the thrombus 200, moves to the proximal side or in the proximal direction, as illustrated in FIG. 4(A), the cutting part 25 comes into contact with the thrombus 200. The cutting part 25 having a ring shape with the three-dimensional shape in the inside thereof receives a part of the thrombus 200, and is thus configured in a way facilitating catching the thrombus 200. A ring-shaped cutting part is better able to catch the thrombus compared to a solid cutting part 25 because the ring-shaped cutting part 25 has a space to catch the thrombus inside. Therefore, the outer edge 26 and/or the inner edge 27 that each function as a cutting blade or cutting edge of the cutting part 25 is not likely to slip with respect to the thrombus 200, and can effectively cut the thrombus 200. In particular, the inner edge 27 that constitutes the cutting blade in the cutting part 25 that is provided at a position distant from the shaft part 21 (a position at an opposite side in the peripheral direction) is effectively caught on the thrombus 200, and can effectively cut the thrombus 200. Cut thrombi (cut object(s)) 201 float in the blood vessel. Subsequently, the aspirating device that is connected to the hub opening portion 35 via the Y connector causes a negative pressure to act on the lumen 34 of the sheath main body 31, thus drawing the cut thrombus toward the proximal end of the sheath 30. Accordingly, the sheath 30 aspirates the floating thrombi 201 from the sheath opening portion 36. The aspirated thrombi 201 are discharged to outside the living body through the lumen 34 and the hub opening portion 35.

When the thrombus 201 floating in the blood vessel is larger than the sheath opening portion 36, the thrombus 201 is not able to enter the lumen 34 but is caught by the sheath opening portion 36. Accordingly, the sheath opening portion 36 is blocked by the large thrombus 200. For solving this blockage, the operator can repeatedly operate the shaft part 21 to move the cutting part 25 toward the sheath opening portion 36 and away from the sheath opening portion 36. When the cutting part 25 moves in the proximal direction and is led into the sheath opening portion 36, the large thrombus 201 that blocks the sheath opening portion 36 is sandwiched between the sheath opening portion 36 and the cutting part 25. The inside of the ring-shaped cutting part 25 receives a part of the thrombus 201 having a three-dimensional shape and is thus easy to be caught by the thrombus 201. Therefore, as illustrated in FIG. 4(B), the outer edge 26 and/or the inner edge 27 that each function as the cutting blade of the cutting part 25 can effectively sandwich the thrombus 201 that blocks the sheath opening portion 36 between the outer edge 26 and/or the inner edge 27 and the sheath opening portion 36, and can cut the thrombus 201. The sandwiched thrombus 201 receives a shear force from the sheath opening portion 36 and the cutting part 25, and is effectively cut. A site at which the shear force of the cutting part 25 is caused to act can be both of or either one of the outer edge 26 and the inner edge 27 that function as the cutting blade. The thrombi 201 having been cut and led into the lumen 34 are aspirated by the aspirating device, and are discharged to outside the body.

Meanwhile, the cutting part 25 is inclined relative to the center axis X of the shaft part 21. Therefore, the cutting part 25 does not come into strong contact with the sheath opening portion 36 but can smoothly enter the sheath opening portion 36. Therefore, the cutting part 25 is not so likely to damage the sheath opening portion 36.

When the cutting part 25 moves to the distal side and is exposed from the sheath opening portion 36, the circulation in the lumen 34, having been partially blocked by the thrombi 201 and the main cutting body part 22, is increased. This recovers the aspiration force at the sheath opening portion 36 at the distal end of the sheath 30. Accordingly, the sheath 30 can excellently aspirate the floating thrombus 200 from the sheath opening portion 36. The aspirated thrombi 201 are discharged to outside the living body through the lumen 34 and the hub opening portion 35. Subsequently, when thrombus 201 larger than the sheath opening portion 36 is aspirated, the thrombus 201 does not enter the lumen 34 but is caught by the sheath opening portion 36. When the cutting part 25 is again led into the sheath opening portion 36, the large thrombus 201 that blocks the sheath opening portion 36 is cut by being sandwiched between the sheath opening portion 36 and the cutting part 25, and is removed.

Subsequently, the operator alternately moves the main cutting body part 22 to the distal side and to the proximal side along the blood vessel. That is, the operator moves the main cutting body part 22 in the distal direction from a position proximal of the thrombus 200 to a position distal of the thrombus, and moves the main cutting body part 22 in the proximal direction from a position distal of the thrombus 200 to a position proximal of the thrombus. This enables the operator to cut, aspirate, and remove the thrombus 201 that is caught at the sheath opening portion 36 while causing the thrombus 201 adhered on the blood vessel to fall off or separate from the blood vessel by the cutting part 25.

After the aspiration and the removal of the thrombi 201 has been completed, the operator stops the aspiration by the aspirating device. Thereafter, the operator extracts the removal device 20 through the sheath 30 to outside the body, and extracts the sheath 30. Accordingly, the procedure of removing the thrombi 200 and 201 is completed.

The removal device 20 in the first embodiment includes: the elongated shaft part 21; and the cutting part 25 that is fixed to the distal portion of the shaft part 21, and the proximal portion of the cutting part 25 includes a ring-ring-shaped cutting blade, and a surface on which the cutting blade is positioned is inclined relative to the center axis X of the shaft part 21 at an angle of less than 90 degrees.

The removal device 20 configured as the above is inserted into a body lumen and then pulled to allow the cutting blade to cut an object such as the thrombus 200. The inside of the cutting blade having a ring shape receives a part of an object having a three-dimensional shape and is thus easy to be caught by the object. Therefore, the removal device 20 can effectively cut and remove the object by the cutting blade, and the cutting blade is difficult to slip with respect to the object. Moreover, the surface on which the cutting blade is positioned is inclined relative to the center axis X of the shaft part 21 at an angle of less than 90 degrees. The cutting blade is thus not likely to damage the sheath 30 when moving to the proximal side. Accordingly, the removal device 20 can suppress damage to another device such as the sheath 30. The cutting blade can be either one or both of the outer edge 26 and the inner edge 27. Accordingly, for example, each of the outer edge and the inner edge of the cutting blade does not need to have a ring shape, but a combination of the outer edge and the inner edge may configure the ring shape. Moreover, the surface on which the cutting blade is positioned is inclined relative to the center axis X of the shaft part 21 at an angle of less than 90 degrees, so that in a case where the cutting blade abuts on the distal surface of the sheath 30, the cutting part 25 is positioned radially outward of the sheath 30. At this time, the contact with the distal surface of the sheath 30 can be further reduced by the surface on which the cutting blade is positioned. Accordingly, the cutting part 25 can be smoothly led into the lumen (the lumen 34, which is described later) of the sheath 30.

Moreover, in the cutting part 25, the concave portion 23 is formed from the proximal end toward the distal side. Therefore, the cutting part 25 having a ring shape, receives a part of the object having a three-dimensional shape in the concave portion 23, and is easy to be caught by the object.

Moreover, the shaft part 21 is fixed to the cutting part 25 at a position spaced in the radial direction from the center axis Y of the cutting part 25. Accordingly, a maximum distance from the center axis X of the shaft part 21 to the cutting part 25 becomes larger than that in a case where the shaft part 21 is positioned at the center axis Y of the main cutting body part 22. Accordingly, the cutting part 25 having a high cut effect can be effectively disposed in the main cutting body part 22 the size of which is limited in order to be inserted into the body lumen. The position spaced from the center axis Y of the cutting part 25 may be, for example, on the outer peripheral surface of the cutting part 25, but may be on the inner peripheral surface of the cutting part 25 or between the outer peripheral surface and the inner peripheral surface.

Moreover, the shaft part 21 is fixed to the proximal end of the cutting blade (the outer edge 26 and the inner edge 27). Accordingly, when the cutting part 25 that penetrates through the sheath 30 and protrudes to the distal side from the sheath 30 moves to the proximal side or in the proximal direction by being pulled by the shaft part 21, the cutting part 25 can smoothly enter the sheath opening portion 36 because the cutting blade is inclined. Accordingly, the cutting part 25 is not caught by the distal end of the sheath 30, thereby improving the operability of the removal device 20.

Moreover, the removal system 10 according to the first embodiment includes: the sheath 30 in which a lumen to cause or convey an aspiration force to act is formed; and the removal device 20 capable of being inserted into the sheath 30, and in the removal system 10, the removal device 20 includes the elongated shaft part 21, and the cutting part 25 that is fixed to the distal portion of the shaft part 21; the proximal portion of the cutting part 25 includes the ring-shaped cutting blade; and a surface on which the cutting blade is positioned is inclined relative to the center axis of the shaft part 21 at an angle of less than 90 degrees.

The removal system 10 configured as above, by positioning the cutting part 25 so that the cutting part 25 is distal of the distal end of the sheath 30 so that the cutting part 25 protrudes distally from the sheath 30 and then pulling the shaft part 21 to the proximal side, can effectively cut an object such as the thrombus 201 that is sandwiched between the sheath opening portion 36 and the cutting blade. The inside of the cutting blade having a ring shape receives a part of an object having a three-dimensional shape, and is thus readily able to catch the object. Therefore, the removal system 10 can effectively cut the object by the cutting blade that is difficult to slip with respect to the object. Accordingly, the removal system 10 can continuously aspirate and remove the object without clogging the sheath 30 with the object. Moreover, the sloped or inclined surface 24 on which the cutting blade is positioned is inclined relative to the center axis X of the shaft part 21 at an angle of less than 90 degrees, so that the cutting blade is difficult to damage the sheath 30 when moving to the proximal side. Accordingly, the removal system 10 can suppress damage to another device such as the sheath 30. The cutting blade can be either one or both of the outer edge 26 and the inner edge 27.

The form of a main cutting body part is not limited to the abovementioned example. For example, FIG. 5(A) illustrates a removal device 40 serving as a first modification example. In this example of the removal device, the main cutting body part 41 may be surrounded by the cutting part 25, and a through-hole 42 that penetrates from the distal end to the proximal end may be formed. In other words, the concave portion that is formed in the embodiment of the cutting part 25 described above is formed so that it penetrates completely through the cutting part. This allows the object cut by the cutting part 25 to come out from both sides of the through-hole 42, so that the object is not so likely to remain in the through-hole 42. Therefore, the removal device 40 can maintain the cut effect long. Moreover, even in a case where the through-hole 42 is clogged with the object, when the main cutting body part 41 enters an inside of the sheath 30, the aspiration force acts on the through-hole 42. Therefore, the object having clogged up the through-hole 42 is moved to the proximal side, and removed. Therefore, the removal device 40 can maintain the cut effect long. In the description above and below, features that are the same or similar to those described previously are identified by the same reference numerals and a detailed description of such features is not repeated.

Figure 5B:
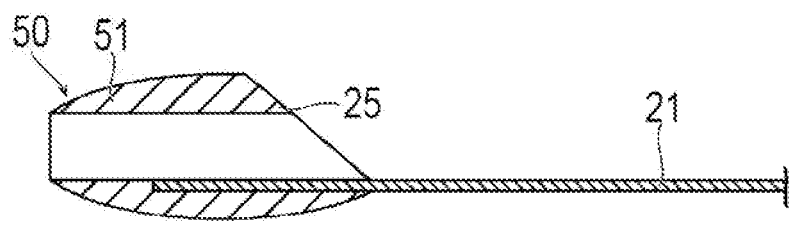

In a removal device 50 serving as a second modification example illustrated in FIG. 5(B), a main cutting body part 51 may include a tubular body having an approximately central portion in the axial direction that possesses an outer diameter that is relatively large. In the illustrated embodiment, the approximately axially central portion of the tubular main cutting body part 51 possesses an outer diameter larger than a remainder of the tubular main cutting body part 51. The shaft part 21 may be fixed to an inner peripheral surface of the main cutting body part 51, instead of the outer peripheral surface of the main cutting body part 51. An outer diameter of a distal portion of the main cutting body part 51 decreases toward the distal side (i.e., in the distal direction toward the left in FIG. 5(B)), and substantially coincides with an inner diameter of the main cutting body part 51 at the distal end. In other words, the thickness of the distal portion of the main cutting body part 51 becomes thinner toward the distal end. Therefore, the main cutting body part 51 can smoothly proceed to the distal side while widening a clearance of a stenosed site of the body lumen.

Figure 5C:
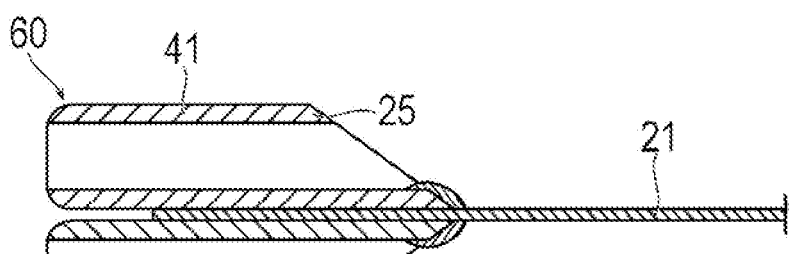

Moreover, in a removal device 60 serving as a third modification example illustrated in FIG. 5(C), two or more main cutting body parts 41 each having a structure similar to that in the abovementioned first modification example shown in FIG. 5(A) may be provided. The plurality of the main cutting body parts 41 are arranged so as to surround the shaft part 21. The removal device 60 can improve the ability to cut the thrombi 200 and 201 because the removal device 60 is provided with the plurality of the main cutting body parts 41.

Figure 5D:
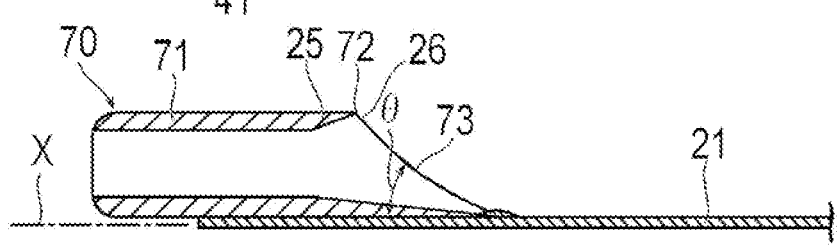

Moreover, in a removal device 70 serving as a fourth modification example illustrated in FIG. 5(D), a main cutting body part 71 may include a sharp cutting blade 72 that protrudes to the proximal side. Accordingly, the cutting blade 72 can be formed sharper than a case where the cutting blade 72 is formed by obliquely cutting the cylinder. In the fourth modification example, the cutting blade 72 is formed on the outer edge 26 that is positioned at an outer peripheral surface side of the main cutting body part 71. Accordingly, an inner diameter of the cutting part 25 spreads or expands in a tapered shape toward the proximal side (i.e., to the right in FIG. 5(D)). This expands a cross-sectional area of the through-hole that is surrounded by the cutting part 25, so that an object serving as a cut target can easily enter the through-hole. Accordingly, the cutting part 25 can excellently cut the object. Moreover, a slope 73 on which the ring-shaped cutting blade 72 is positioned does not need to be a plane, but may be a curved surface, for example. An inclined angle θ of the slope 73 relative to the center axis X of the shaft part 21 may become larger (i.e., may increase) apart farther distances from the shaft part 21 in a direction orthogonal to the center axis X of the shaft part 21. Accordingly, the cutting part 25 is able to rather easily catch an object, and can excellently cut the object.

Figure 5E:
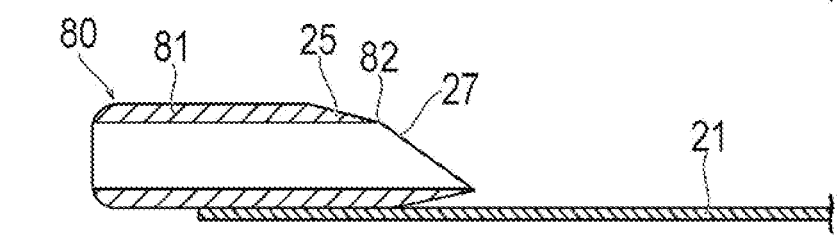

Moreover, in a removal device 80 serving as a fifth modification example illustrated in FIG. 5(E), a cutting blade 82 of a main cutting body part 81 may be formed on the inner edge 27 that is positioned at an inner peripheral surface side of the main cutting body part 81. Accordingly, the outer diameter of the cutting part 25 decreases in a tapered shape toward the proximal side (i.e., toward the right in FIG. 5E). This makes the cutting blade 82 difficult to come into contact with the sheath opening portion 36, so that it is possible to suppress damage to the sheath 30. The cutting blade may be disposed at a position (for example, between the inner peripheral surface and the outer peripheral surface) different from the inner peripheral surface and the outer peripheral surface of the main cutting body part.

Second Embodiment

Figure 6:
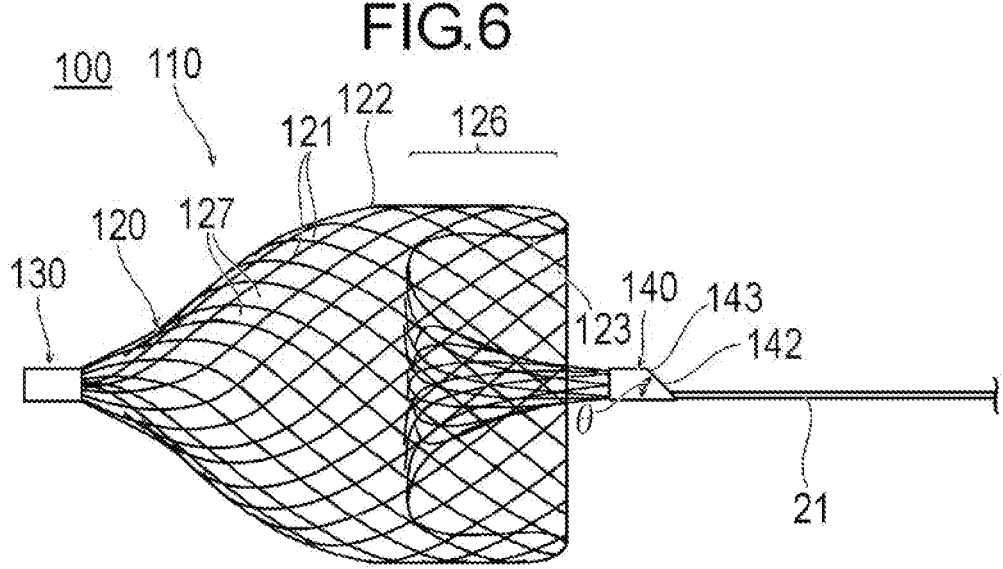
FIG. 6 is a plan view illustrating a removal device in a second embodiment.
Figure 7:
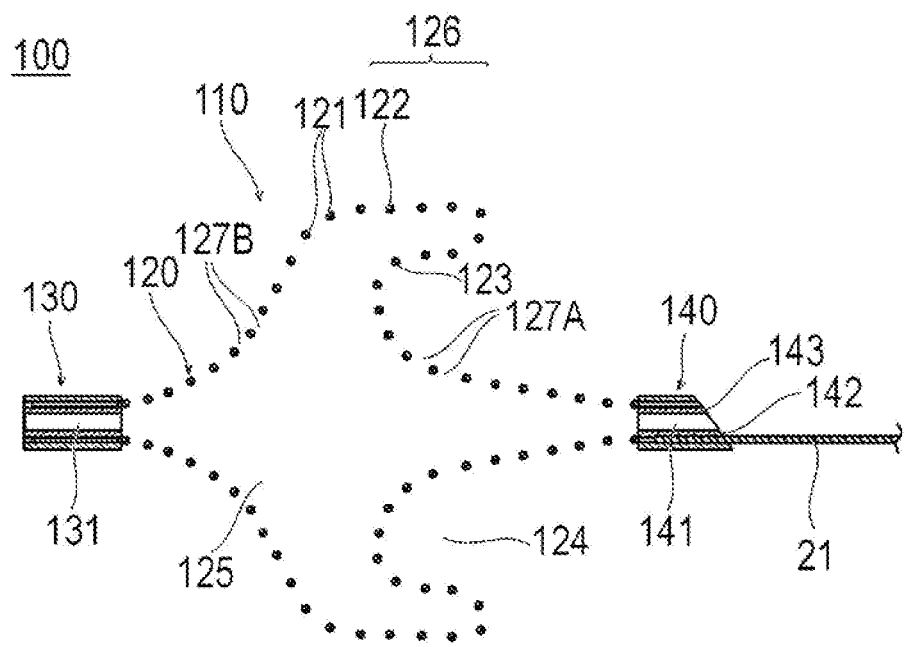
FIG. 7 is a cross-sectional view illustrating the removal device in the second embodiment.

A removal system 100 according to a second embodiment differs from the first embodiment in that, as illustrated in FIGS. 6 and 7, an expandable part 120 capable of expanding (automatically expanding) in a radial direction (a direction orthogonal to the center axis X of the shaft part 21) is provided at the distal side from a cutting part 143. In the description below, features that are the same or similar to those described above are identified by the same reference numerals and a detailed description of such features is not repeated.

The removal system 100 according to the second embodiment is provided with a removal device 110 and the sheath 30 (see FIG. 1). The removal device 110 is provided with the expandable part 120 and the shaft part 21.

The expandable part 120 is a filter that collects an object such as the thrombi 201 flowing with the blood. The expandable part 120 is provided with a plurality of linear bodies 121 that are braided in a net shape so as to form a tubular body and are flexibly deformable, a distal side interlock portion 130, and a proximal side interlock portion 140 (main cutting body part) that is interlocked or fixed to the shaft part 21. The plurality of the linear bodies 121 include gaps 127 among or between the linear bodies 121 by virtue of being braided.

The distal side interlock portion 130 pinches and fixes distal ends of the plurality of the linear bodies 121 between two coaxial and axially overlapping tubular bodies or tubes. The distal side interlock portion 130 includes a distal side through-hole 131 that penetrates from the distal end to the proximal end. The distal side through-hole 131 may allow the guide wire to be inserted thereinto. The distal side through-hole 131 does not need to be formed.

The proximal side interlock portion 140 pinches and fixes proximal ends of the plurality of the linear bodies 121 and the distal end of the shaft part 21 between two coaxial and axially overlapping tubular bodies or tubes. In the proximal side interlock portion 140, a proximal side through-hole 141 that penetrates from the distal end to the proximal end is formed. The proximal side through-hole 141 may allow the guide wire to be inserted thereinto. A proximal end portion of the proximal side interlock portion 140 includes a slope (sloping surface) 142 that is inclined at an angle θ of more than zero degrees and of less than 90 degrees relative to the center axis X of the shaft part 21. A ring-shaped region that surrounds the proximal side through-hole 141 of the slope 142 forms the cutting part 143. Accordingly, the slope 142 is a surface on which or at which the cutting blade is positioned.

In a natural state where no external force acts, the expandable part 120 is in a turned back state where a part of the expandable part 120 is turned back on itself in the axial direction by the self-elastic force (restoring force) of the linear bodies 121. When the expandable part 120 is in the turned back state, the proximal side interlock portion 140 and the distal side interlock portion 130 approach each other. In turned back state, the expandable part 120 is provided with a first section 122 that is interlocked to the distal side interlock portion 130, and a second section 123 that is interlocked to the proximal side interlock portion 140. The second section 123 has entered or is positioned in an interior of the first section 122. In an interior of the expandable part 120, an internal space 125 is formed. The second section 123 has a concave shape that is open to the proximal side to form a collecting space 124 in which the thrombus 200 or the like is collected. The first section 122 includes a large-diameter portion 126 having an approximately constant outer diameter within a prescribed range in the axial direction, in the vicinity of the second section 123. The large-diameter portion 126 is a section having an approximately maximum outer diameter of the expandable part 120. A gap 127b in the first section 122 is larger than a gap 127A in the second section 123.

The number of the linear bodies 121 is not specifically limited, and may be 4 to 72, for example. Moreover, the condition of the braiding of the linear bodies 121 is not specifically limited. The outer diameter of the linear body 121 is selectable as appropriate in accordance with the material of the linear body 121 and the usage purpose of the expandable part 120, and may be 20 to 300 μm, for example.

A constituent material from which the linear bodies 121 may be fabricated is preferably a material having flexibility. Examples of the material from which the linear bodies 121 may be fabricated include a shape memory alloy to which the shape memory effect and the super elasticity are applied by thermal treatment, stainless steel, tantalum (Ta), titanium (Ti), white silver (Pt), gold (Au), tungsten (W), polyolefin such as polyethylene or polypropylene, polyamide, polyester such as polyethylene terephthalate, fluorinated polymer such as tetrafluoroethylene-ethylene copolymer (ETFE), polyether ether ketone (PEEK), polyimide.

Constituent materials from which the distal side interlock portion 130 and the proximal side interlock portion 140 may be fabricated are not specifically limited. For example, stainless steel, polyether ether ketone (PEEK), and the like can be suitably used.

The expandable part 120 is elastically deformed or collapsed by being accommodated in the sheath 30 as illustrated in FIG. 8(A) to become in a collapsed state in which the outer diameter is small. When the expandable part 120 is in the collapsed state, the proximal side interlock portion 140 and the distal side interlock portion 130 are axially spaced apart from each other.

When the expandable part 120 is released from the sheath 30, the expandable part 120 expands and is indwelt in the blood vessel in a shape close to the natural state as illustrated in FIG. 8(B). At this time, the large-diameter portion 126 comes into contact with the blood vessel wall. The inflating part 120 is actually indwelt in the blood vessel wall in a state of being collapsed to a greater extent in the radial direction than the natural state of the inflating part 120 so as to generate an outward pressing force with respect to the blood vessel wall by a self-expanding force. The large-diameter portion 126 comes into contact with the blood vessel wall over a wide area because the large-diameter portion 126 has a length to some extent in the axial direction. Therefore, the large-diameter portion 126 is firmly fixed to the blood vessel wall.

The expandable part 120 does not need to be in a turned back state immediately after being released from the sheath main body 31 in the blood vessel. In this case, after the expandable part 120 has been indwelt in the blood vessel, the sheath main body 31 may push the expandable part 120 to the distal side or in the distal direction. Moreover, a dilator or another sheath is used to push the expandable part 120 to the distal side or in the distal direction. Accordingly, the second section 123 of the expandable part 120 enters an inner side of the first section 122, and the expandable is in a turned back state.

The expandable part 120 acts as a filter and collects, as illustrated in FIG. 9, the thrombi 201 having been destroyed or cut-up by a device that is separately provided in the blood vessel. The thrombi 201 are collected in the collecting space 124 and the internal space 125. Subsequently, the aspirating device that is connected to the sheath 30 causes a negative pressure to act on the lumen 34 of the sheath main body 31. Accordingly, the sheath 30 aspirates the thrombi 201 collected in the collecting space 124 from the sheath opening portion 36. The aspirated thrombi 201 are discharged to the outside of the living body through the lumen 34.

In addition, the operator operates the shaft part 21 to alternately move the proximal side interlock portion 140 to the proximal side (in the proximal direction) and the distal side (in the distal direction) along the blood vessel. Accordingly, the second section 123 of the inflating part 120 moves to the distal side and to the proximal side with respect to the first section 122. Therefore, the thrombi 201 having been adhered to the inflating part 120 by the blood flow are separated from the inflating part 120. Accordingly, the sheath 30 can effectively aspirate the thrombi 201.

Moreover, the expandable part 120 is in a turned back state, so that the second section 123 that is positioned at the inner side is easy to move to the proximal side and the distal side with respect to the first section 122 fixed to the blood vessel. This makes it easy to move the proximal side interlock portion 140 to the proximal side and the distal side. Moreover, when the range where the first section 122 and the second section 123 overlap with each other is long in the axial direction, the proximal side interlock portion 140 is capable of moving long to the proximal side and the distal side. When the proximal side interlock portion 140 moves to the proximal side, the cutting part 143 cuts the large thrombus 201 that blocks the sheath opening portion 36, and leads the cut thrombi 201 into the sheath 30. Accordingly, the sheath 30 can excellently continue the aspirating of the thrombi 201.

Moreover, the operator may operate not only the shaft part 21 but may also alternately move the sheath 30 to the proximal side and the distal side along the blood vessel. The sheath 30 moves to the distal side to allow the cutting part 143 of the proximal side interlock portion 140 to enter the sheath opening portion 36 while cutting the thrombus 201.

After the aspirating of the thrombus 200 by the sheath 30 has been completed, the operator pushes the sheath 30 to the distal side or in the distal direction while holding the position of the shaft part 21. Accordingly, the proximal side interlock portion 140 is separated from the distal side interlock portion 130 while entering an interior of the sheath 30. Further, the expandable part 120 is moved to a collapsed state illustrated in FIG. 8(A). Thereafter, the operator extracts the removal device 110 together with the sheath 30 from the blood vessel, and completes the procedure.

The second embodiment of the removal device 110 includes the expandable part 120 capable of expanding, and the expandable part 120 is positioned at the distal side from the cutting part 143. Accordingly, the removal device 110 can aspirate and remove the thrombus 200 while suppressing the object flowing in the body lumen from flowing downstream by the expanding expandable part 120. The expandable part 120 may be directly interlocked to the shaft part 21, or may be interlocked to the shaft part 21 via the cutting part 143.

Moreover, the expandable part 120 includes gaps 127A at the proximal side, and gaps 127B at the distal side larger than the gaps 127A at the proximal side. This allows the small thrombus 201 having passed through the gap 127A at the proximal side to be released downstream from the gap 127B at the distal side. Accordingly, the inflating part 120 can suppress the thrombi 201 from remaining in the internal space 125, and is easy to be collapsed and recovered into the sheath 30.

Moreover, the expandable part 120 can be turned back, and the first section 122 that is not turned back includes the gaps 127B larger than the gaps 127A of the turned-back second section 123. This allows the small thrombus 201 having passed through the gap 127A of the turned-back second section 123 to be released downstream from the gap 127B of the first section 122 that is not turned back. Accordingly, the expandable part 120 can suppress the thrombi 201 from remaining in the internal space 125, and is easy to be collapsed and recovered into the sheath 30.

The form or configuration of the expandable part is not limited to the abovementioned example. For example, in a removal device 150 serving as a sixth modification example illustrated in FIG. 10(A), an expandable part 151 including the plurality of the linear bodies 121 may be provided with at least one release opening portion 152 having a gap in the mesh larger than the gaps 127A and the gaps 127B, at the distal side. Therefore, the thrombi 201 having passed through the gaps 127A and entered the internal space 125 of the inflating part 151 can be released from the release opening portion 152, as illustrated in FIG. 10(B). The thrombi 201 having entered the internal space 125 are the small thrombi 201 having passed through the gaps 127A, so that such thrombi 201 flowing downstream hardly affect the living body. The expandable part 151 releases the thrombi 201 in the internal space 125, and is easy to be collapsed and recovered into the sheath 30.

In a removal device 160 serving as a seventh modification example illustrated in FIG. 11(A), an expandable part 161 does not need to have a turned back shape in the natural state in which no external force is acted.

In a removal device 170 serving as an eighth modification example illustrated in FIG. 11(B), an expandable part 171 may be a balloon capable of inflating by a fluid being supplied from a balloon hub 172. The fluid having flowed from the balloon hub 172 flows into the expandable part 171 through a lumen of a hollow shaft part 173. The expandable part 171 closes the blood vessel, and suppresses the thrombi 201 from flowing downstream. Accordingly, after the expandable part 171 is indwelt in the blood vessel wall, by using the deformation of the expandable part 171, the main cutting body part 41 including the cutting part 25 can be moved in the axial direction.

This invention is not limited to the above-described embodiments. Various changes by those skilled in the art can be made within the technical scope of this invention. For example, in the abovementioned embodiments, a structure in which the removal system is accessed to a target lesion from the upstream side of the target lesion is employed, however, a structure in which the removal system is accessed to a target lesion from the downstream side thereof may be employed. Moreover, the body lumen into which the removal device is inserted is not limited to the blood vessel, but may be the vessel, the ureter, the bilary duct, the oviduct, or the hepatic duct, for example.

Moreover, in the ring-shaped cutting part, no blade may be formed on a part in the peripheral direction (for example, a section to which the shaft part is fixed). Moreover, the ring-like cutting part does not need to be a perfect ring over 360 degrees, but a slit that extends in the axial direction may be formed, for example. Moreover, the blade of the cutting part may include saw-like asperities, for example.

The detailed description above describes embodiments of an object removal device, object removal system and operational method representing examples of the inventive object removal device, object removal system and operational method disclosed here. The invention is not limited, however, to the precise embodiments and variations described. Various changes, modifications and equivalents can be effected by one skilled in the art without departing from the spirit and scope of the invention as defined in the accompanying claims. It is expressly intended that all such changes, modifications and equivalents which fall within the scope of the claims are embraced by the claims.

What is claimed is:

1. A removal device, comprising:
an elongated shaft part possessing a proximal portion and a distal portion at opposite axial ends of the elongated shaft part, the elongated shaft part possessing a center axis and being axially movable;
a cutting part that is fixed to the distal portion of the shaft part so that the cutting part and the elongated shaft part move together when the elongated shaft part is axially moved, the cutting part including a distal portion and a proximal portion, the proximal portion of the cutting part being positioned axially closer to the proximal portion of the elongated shaft part than the distal portion of the cutting part;
the proximal portion of the cutting part including a ring-shaped cutting blade, the cutting blade being positioned on a surface that is inclined relative to the center axis of the elongated shaft part at an angle of more than 0 degrees and less than 90 degrees; and
an expandable part fixed to the cutting part, the expandable part extending distally beyond a distal end of the cutting part.

2. The removal device according to claim 1, wherein the cutting part includes a hollow portion that is open at both a proximal end and a distal end.

3. The removal device according to claim 1, wherein the elongated shaft part is fixed at a position spaced in a radial direction from center axis of the cutting part.

4. The removal device according to claim 1, wherein the shaft part is fixed to a proximal end of the cutting blade.

5. The removal device according to claim 1, wherein the expandable part includes spaced apart gaps at a proximal portion of the expandable part and spaced apart gaps at a distal portion of the expandable part, at least some of the gaps at the distal portion of the expandable part being larger than at least some of the gaps at the proximal portion of the expandable part.

6. The removal device according to claim 5, wherein a section of the expandable part is a turned back section that is configured to be turned back on itself and an other section of the expandable part is configured to not be turned back on itself, and
the gaps at the distal portion of the expandable part that are larger than at least some of the gaps at the proximal portion of the expandable part are located at the other section of the expandable part that is configured to not be turned back on itself.

7. A removal system comprising:
an elongated sheath that includes a lumen possessing an open distal end and an open proximal end, the lumen being connectable to an aspirating device that produces an aspiration force in the lumen;
an elongated shaft part possessing a proximal portion and a distal portion at opposite axial ends of the elongated shaft part, the elongated shaft part possessing a center axis, the elongated shaft part being positionable in the lumen of the elongated sheath and being axially movable relative to the elongated sheath; and
a cutting part that is fixed to the distal portion of the elongated shaft part so that the cutting part and the elongated shaft part move together when the elongated shaft part is axially moved, the cutting part including a distal portion and a proximal portion, the proximal portion of the cutting part being positioned axially closer to the proximal portion of the elongated shaft part than the distal portion of the cutting part,
the proximal portion of the cutting part including a ring-shaped cutting blade, the cutting blade being positioned on a surface that is inclined relative to the center axis of the elongated shaft part at an angle of more than 0 degrees and less than 90 degrees, and
an expandable part that is expandable from a collapsed state to an expanded state, the expandable part being fixed to the cutting part and extending distally beyond a distal end of the cutting part.

8. The removal system according to claim 7, wherein the cutting part includes a hollow portion that extends in a proximal direction from the cutting blade, the hollow portion being open at a proximal end of the hollow portion and being open at a distal end of the hollow portion.

9. The removal system according to claim 7, wherein the cutting part includes a center axis, the elongated shaft part being fixed to the cutting part at a position such that the center axis of the elongated shaft part and the center axis of the cutting part are not coaxial.

10. The removal system according to claim 7, wherein the distal portion of the cutting part extends distally beyond a distal end of the elongated shaft part, the cutting part being cylindrical and the distal portion of the cutting part including rounded corners.

11. A removal device, comprising:
an elongated shaft part possessing a proximal portion and a distal portion at opposite axial ends of the elongated shaft part, the elongated shaft part possessing a center axis;
a cutting part that is fixed to the distal portion of the shaft part, the cutting part including a distal portion and a proximal portion;
the proximal portion of the cutting part including a ring-shaped cutting blade, a proximal end of the cutting blade being a surface that is inclined relative to the center axis of the elongated shaft part at an angle of more than 0 degrees and less than 90 degrees; and
an expandable part fixed to the cutting part, the expandable part being positioned distal to the surface of the cutting blade.

* * * * *